United States Patent
Yu et al.

(10) Patent No.: US 11,480,503 B2
(45) Date of Patent: Oct. 25, 2022

(54) METHOD FOR REDUCING INTRACELLULAR NON-SPECIFIC STAINING CAUSED BY METAL COMPLEX

(71) Applicant: SEOUL NATIONAL UNIVERSITY R&DB FOUNDATION, Seoul (KR)

(72) Inventors: Junhua Yu, Seoul (KR); Sungmoon Choi, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 558 days.

(21) Appl. No.: 16/489,779

(22) PCT Filed: Mar. 2, 2017

(86) PCT No.: PCT/KR2017/002267
§ 371 (c)(1),
(2) Date: Aug. 29, 2019

(87) PCT Pub. No.: WO2018/159875
PCT Pub. Date: Sep. 7, 2018

(65) Prior Publication Data
US 2020/0011771 A1   Jan. 9, 2020

(51) Int. Cl.
*G01N 1/30* (2006.01)

(52) U.S. Cl.
CPC .......... *G01N 1/30* (2013.01); *G01N 2001/302* (2013.01)

(58) Field of Classification Search
CPC ...................... G01N 1/30; G01N 2001/302
See application file for complete search history.

(56) References Cited

U.S. PATENT DOCUMENTS

| 6,316,267 B1 | 11/2001 | Bhalgat et al. |
| 2010/0081130 A1 | 4/2010 | Lee et al. |

FOREIGN PATENT DOCUMENTS

KR   10-2007-0029030 A   3/2007

OTHER PUBLICATIONS

Montgomery et al., Cell-Penetrating Metal Complex Optical Probes: Targeted and Responsive Systems Based on Lanthanide Luminescence Accounts of Chemical Research 42(7) : 925-937 (Year: 2009).*
Wang et al., A Heterodinuclear Complex Oslr Exhibiting Near-Infrared Dual Luminescence Lights Up the Nucleoli of Living Cells. Organometallics 33: 2681-2684 (Year: 2014).*
Choi, Sung Moon et al., "Tailoring Silver Nanodots for Intracellular Staining", Photochemical & Photobiological Sciences, vol. 10, No. 1, pp. 109-115 (Jan. 2011) See abstract; "Results and discussion" section. 13 pages.
Lim, Mark J. et al., "A Luminescent Europium Complex for the Sensitive Detection of Proteins and Nucleic Acids Immobilized on Membrane Supports", Analytical Biochemistry, vol. 245, pp. 184-195 (1997) See abstract. 70 pages.
Yu, Junhua et al., "Shuttle-based Fluorogenic Silver-cluster Biolabels", Angewandte Chemie (International ed. in English), vol. 48, pp. 318-320 (2009), See pp. 318 and 319. 3 pages.
International Search Report for PCT/KR2017/002267 dated Nov. 30, 2017, 2 pages.

* cited by examiner

*Primary Examiner* — Ethan C Whisenant
(74) *Attorney, Agent, or Firm* — Kilpatrick Townsend & Stockton LLP

(57) ABSTRACT

The present invention relates to a method for reducing intracellular non-specific staining caused by a metal complex, and a method for improving specific staining. When a cell is stained by the method of the present invention, intracellular non-specific staining, which inevitably occurs when a metal complex is used, can be minimized, and as a result, specific staining for a target organelle can be effectively induced.

10 Claims, 6 Drawing Sheets
Specification includes a Sequence Listing.

METHOD FOR REDUCING INTRACELLULAR NON-SPECIFIC STAINING CAUSED BY METAL COMPLEX

REFERENCE TO A SEQUENCE LISTING

The Sequence Listing written in file 2022-06-01_Sequence_Listing_1153596-KD-56225-US, created Jun. 1, 2022, which is 1 Kb in size, machine format IBM-PC, MS-Windows operating system, is hereby incorporated by reference in its entirety for all purposes.

TECHNICAL FIELD

The present disclosure relates to a method of reducing intracellular non-specific staining caused by a metal complex, and a method of improving specific staining.

More specifically, the present disclosure relates to a method capable of reducing non-specific staining by identifying the cause of the intracellular non-specific staining due to the metal complex and by removing the same.

Further, the present disclosure relates to a method of improving specific staining, to which the technical spirit derived from the method of reducing non-specific staining is applied.

BACKGROUND ART

Metal complexes such as gold nanoclusters or silver nanoclusters have been frequently used in the biotechnology field owing to their optical properties and have received much attention as alternatives to organic dyes.

Specifically, the biotechnology field where metal complexes are utilized may be exemplified by the cell imaging field such as intracellular specific staining, etc.

Metal complexes used in the cell imaging field may improve fluorescence efficiency or ease of tracking by changing a length or kind of a ligand in the complex or by improving a method of preparing the complex.

Meanwhile, a strong interaction occurs between a metal complex and a biomacromolecule, resulting in non-specific staining in other sites as well as in an intended site. For example, at the time of staining the intracellular nucleolus, non-specific staining may be caused by metal complexes in the cytoplasm or karyoplasm in addition to the nucleolus, resulting in a low signal-to-noise ratio (S/N ratio) for the nucleolus staining.

Accordingly, there is a demand for the development of the technology capable of reducing the non-specific staining whereas to induce the specific staining of the target cellular organelles in the bioimaging field where metal complexes are utilized.

DESCRIPTION OF EMBODIMENTS

Technical Problem

An object of the present disclosure is to provide a method of effectively reducing non-specific staining by identifying the cause of the non-specific staining when a metal complex that exhibits nucleolus binding ability is used, in which the non-specific staining inevitably occurs in cellular staining when the metal complex is used as a fluorescent-labeling material, and then by removing the cause.

Another object of the present disclosure is to provide a method of improving specific staining, to which the technical spirit derived from the method of reducing non-specific staining is applied.

Still another object of the present disclosure is to provide a method of effectively improving intracellular specific staining while maintaining excellent optical properties of metal complexes as much as possible.

Solution to Problem

To solve the above objects, the present disclosure relates to a method of reducing intracellular non-specific staining and a method of improving specific staining.

The method of reducing intracellular non-specific staining may include blocking intracellular active sites by oxidizing intracellular sulfhydryl groups, wherein effectiveness of the blocking is demonstrated according to intracellular staining of the nucleolus by a metal complex that shows a specific staining ability for the intracellular nucleolus.

In one embodiment, the metal complex may be a silver nanocluster containing 5'-CGCGC$_{12}$CGCG-3' (SEQ ID NO:1) as a protecting group.

In one embodiment, the blocking of the intracellular active sites may include converting the sulfhydryl groups into disulfides using potassium hexacyanoferrate(III), potassium periodate, osmium tetraoxide, or iodine.

Further, the present disclosure relates to a method of improving intracellular specific staining, to which the technical spirit derived from the method of reducing non-specific staining is applied.

In other words, the method of improving intracellular specific staining may include blocking intracellular active sites by oxidizing intracellular sulfhydryl groups and inducing staining of intracellular specific sites by a metal complex.

In one embodiment, the metal complex may include a transition metal or a member of the lanthanides group.

In one embodiment, the metal complex may include a metal core; and a ligand protecting the metal core.

In one embodiment, the ligand may be a peptide, DNA, ssDNA, biotinylated ssDNA, a cyclen derivative, a bipyridine derivative, or a terpyridine derivative.

In one embodiment, when the ligand is biotinylated ssDNA, the method may further include labelling the cellular target with a biotinylated antibody in cells and tagging avidin, wherein the blocking of intracellular active sites may be performed after the labelling and before the tagging.

In one embodiment, the method of improving the intracellular specific staining may further include permeating the cells with a surfactant.

Advantageous Effects of Disclosure

The present disclosure may provide a method capable of effectively reducing non-specific staining by identifying a major cause of intracellular non-specific staining.

Further, the present disclosure may provide a method of effectively improving specific staining by applying the technical spirit which is derived from the method of reducing non-specific staining.

Further, the present disclosure may provide a method of effectively improving intracellular specific staining while maintaining excellent optical properties of metal complexes as much as possible. Therefore, application fields of the metal complexes may be extended to biomarkers, cell imaging, etc.

However, the scope of the present disclosure is not limited to these effects.

Figure 3:
Figure 4:
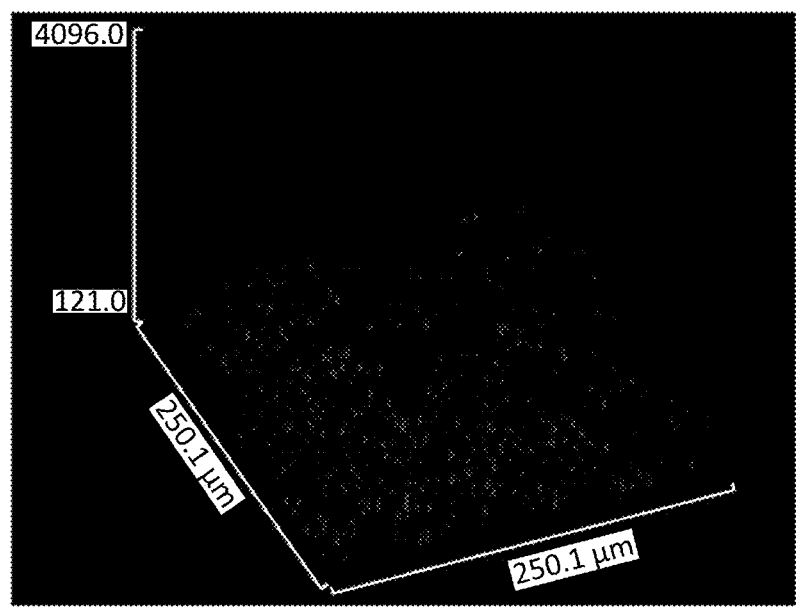
Figure 5:
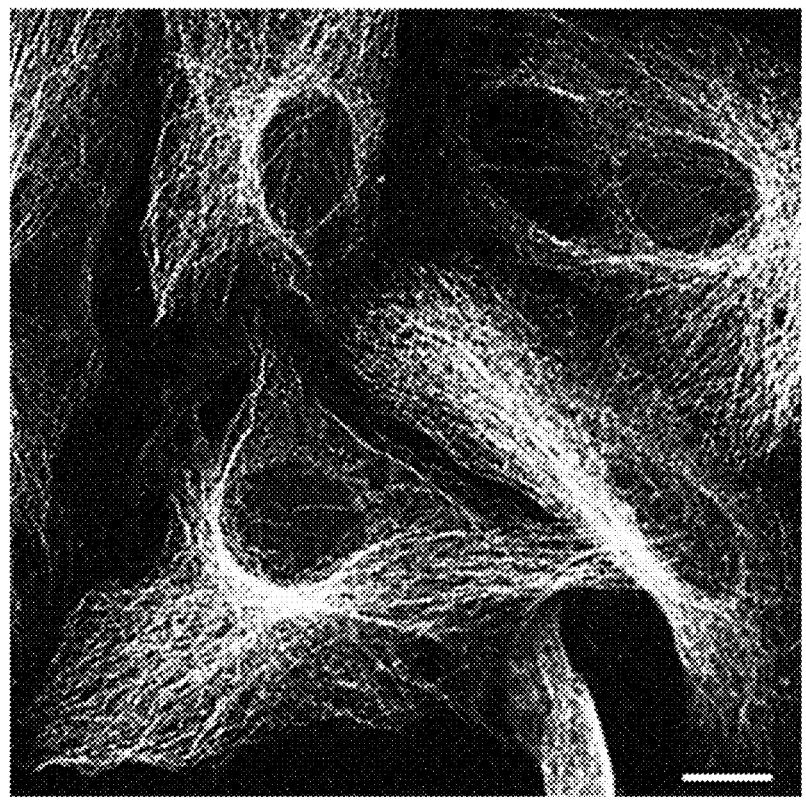
Figure 6:
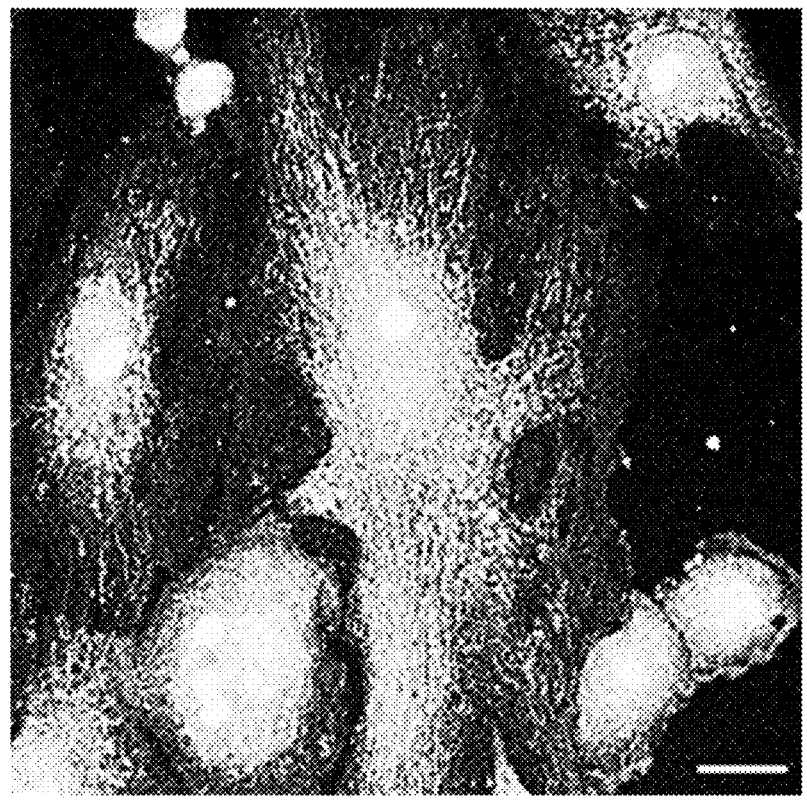

FIGS. 3 and 4 show results of intracellular staining employing blocking according to Example 1 of the present disclosure;

FIG. 5 shows a result of intracellular staining according to Example 2 of the present disclosure; and FIG. 6 shows a result of intracellular staining according to Comparative Example 2 of the present disclosure.

BEST MODE

Hereinafter, the present disclosure will be described in more detail.

As used herein, the singular forms are intended to include plural forms as well, unless the context clearly indicates otherwise.

The terms "comprises" and "comprising", as used herein, specify the presence of stated features, integers, steps, operations, elements, components, and/or groups, but do not preclude the presence or addition of one or more other features, integers, operations, elements, components, and/or groups.

As used herein, the term "sulfhydryl group" means a thiol group (—SH) presenting in a cysteine residue of a protein, and the term "disulfide" means an S—S bond formed by oxidation of the sulfhydryl group or a compound containing the bond.

In cellular staining using metal complexes, non-specific staining generally occurs due to intracellular proteins and metal complexes, and a signal-to-noise ratio for an actual target cellular organelle is low, and as a result, it is difficult to obtain a signal from the actual target.

To solve this problem, there has been a blocking method of reducing non-specific staining using bovine serum album (BSA).

However, since BSA is also a kind of protein, it may induce non-specific staining in cellular staining when metal complexes are used as staining agents, and it may not effectively perform the blocking function.

Accordingly, the present inventors recognized that a major cause of intracellular non-specific staining is an interaction between a metal complex and a sulfhydryl group in a protein of a cell, and they found that intracellular non-specific staining may be reduced by blocking intracellular active sites through oxidation of the sulfhydryl groups, thereby completing the present disclosure.

Particularly, the present inventors examined whether the above blocking may reduce the intracellular non-specific staining by applying a metal complex capable of specifically staining the nucleolus in a cell. Specifically, the present inventors derived the technical meaning of the blocking through cell staining results of the metal complex according to whether or not the blocking is applied.

Further, the present inventors invented a method of effectively inducing specific staining of the metal complex by applying the technical spirit which is derived from the method of reducing non-specific staining.

The present disclosure relates to a method of reducing intracellular non-specific staining.

The method of reducing intracellular non-specific staining may include blocking intracellular active sites by oxidizing intracellular sulfhydryl groups, wherein effectiveness of the blocking is demonstrated according to intracellular staining of cells with a metal complex having a specific staining ability for the intracellular nucleolus.

In the present disclosure, a metal complex having a specific staining ability for the nucleolus was utilized as an example of the metal complex in the method of reducing non-specific staining.

In detail, as in Example 1 and Comparative Example 1 of the present disclosure described below, a silver nanocluster (hereinafter, referred to as "615-emitter") that is protected with 5'-CGCGC$_{12}$CGCG-3' (SEQ ID NO:1) and exhibits a specific nucleolus-binding ability was used to induce intracellular staining, and characteristics of the staining were compared according to whether or not the blocking is applied. As a result, it was confirmed that a major cause of the intracellular non-specific staining is a bond between the metal complex and a sulfhydryl group in a protein of a cell.

Meanwhile, the blocking of the intracellular active sites by oxidizing the intracellular sulfhydryl groups may include converting the sulfhydryl groups into disulfides using an oxidizing agent.

Specifically, the blocking of the intracellular active sites by oxidizing the intracellular sulfhydryl groups may include converting the sulfhydryl groups into disulfides using potassium hexacyanoferrate(III), potassium periodate, osmium tetroxide, or iodine.

When the blocking is performed, the sulfhydryl groups are converted into disulfides, and the intracellular nucleolus-specific binding ability of the metal complex such as 615-emitter is lost. As a result, it was derived that the blocking of the intracellular active sites by oxidation of the sulfhydryl groups may be a technical feature capable of reducing intracellular non-specific binding and increasing specific binding.

Further, the present disclosure relates to a method of improving specific staining, to which the technical spirit derived from the method of reducing non-specific staining is applied.

The method of improving intracellular specific staining according to the present disclosure is a method of staining using metal complexes, wherein a major technical feature of the method is to include blocking intracellular active sites by oxidation of intracellular sulfhydryl groups before staining of intracellular specific sites with the metal complexes, thereby effectively staining the intracellular specific sites with the metal complexes.

In other words, the method of improving intracellular specific staining according to the present disclosure may include blocking the intracellular active sites by oxidation of the intracellular sulfhydryl groups; and inducing staining of the intracellular specific sites with the metal complexes.

The blocking may be performed using an oxidizing agent which is able to oxidize the intracellular sulfhydryl groups, as described above, and a specific kind of the oxidizing agent is also the same as described above.

Meanwhile, a conversation rate of the intracellular sulfhydryl groups into disulfides and a staining rate of the intracellular specific sites with the metal complexes may vary depending on the kind or concentration of the oxidizing agent exemplified above and the reaction time. In some cases, intracellular staining of the metal complexes may not be induced. Therefore, taking into consideration the concentration of the metal complex, the concentration of the oxidizing agent, or the oxidization time of cells may be determined.

In one embodiment, when no permeation process is performed, the conversion of the sulfhydryl groups into disulfides may be performed at a potassium hexacyanoferrate(III) concentration of 10 mM or less for about 20 minutes, and when a permeation process by a surfactant is performed, the conversion may be performed at a potassium hexacyanoferrate(III) concentration of 100 mM for about 20 minutes.

Further, the method of improving intracellular specific staining according to the present disclosure may include washing the oxidizing agent. The washing of the oxidizing agent may be performed using, for example, a phosphate buffer solution.

The phosphate buffer solution may be, for example, a phosphate buffer solution having a phosphate concentration of 10 mM to 100 mM.

Further, the phosphate buffer solution may be a phosphate buffer solution of pH 7 to pH 8.

The cells used in the blocking may be those previously fixed. The fixing of the cells may be performed using, for example, alcohol, a formaldehyde solution, etc., at a general refrigeration temperature, for example, 4° C. for 10 minutes to 20 minutes.

Further, the method of improving intracellular specific staining according to the present disclosure may include inducing staining of the intracellular specific sites using metal complexes.

The metal complex may include, for example, a metal core; and a ligand protecting the metal core.

Specifically, the metal core may include a transition metal or a member of the lanthanides group.

More specifically, the transition metal may be exemplified by gold, silver, platinum, ruthenium, etc., and the member of the lanthanides group may be exemplified by europium, etc., but is not limited thereto.

The ligand of the metal complex may determine physical properties of the metal complex and a specific intracellular binding site. Therefore, a proper kind of the ligand may be selected by considering physical properties of the complex, a target organelle, etc.

In one embodiment, the ligand may be a peptide, DNA, ssDNA, biotinylated ssDNA, a cyclen derivative, a bipyridine derivative, or a terpyridine derivative.

Meanwhile, a kind of the peptide, DNA, ssDNA, or biotinylated ssDNA which may bind with the metal core of the metal complex is known in the art, and those skilled in the art may use a known peptide, DNA, ssDNA, or biotinylated ssDNA in the present disclosure without limitation.

The metal complex may have, for example, optical properties. More specifically, the metal complex may have fluorescent properties.

In one embodiment, the metal complex may have a luminescence center wavelength within the range of 380 nm to 800 nm.

Meanwhile, when the ligand of the metal complex of the present disclosure is biotinylated ssDNA, the method of improving intracellular specific staining according to the present disclosure may further include labelling a biotinylated antibody in the cell; and tagging avidin. In this regard, the above-described blocking may be performed after the labelling and before the tagging.

In other words, when the method of improving intracellular specific staining using the metal complex according to the present disclosure is induced by biotin-avidin binding, labelling the target with the biotinylated antibody in the cells and tagging of avidin may be performed to induce binding of the metal complex including biotinylated ssDNA to the biotinylated antibody in the cells via avidin.

The labelling of the biotinylated antibody in the cells may be performed using one or two or more of the biotinylated antibody.

Specifically, labelling the target with the biotinylated antibody in the cells may include labelling the target with a biotinylated primary antibody in the cells and labelling the target with a primary antibody with a primary antibody and then labeling the primary antibody with a biotinylated secondary antibody. Further, the method of improving intracellular specific staining of the present disclosure may include the above-described blocking between the above procedures, specifically, the labelling and the tagging, thereby effectively improving the intracellular specific staining.

Further, the method of improving intracellular specific staining according to the present disclosure may further include permeating the cells with a surfactant. When the cells is permeated, the effect of the intracellular specific staining may be further enhanced.

The surfactant is not particularly limited, and for example, a non-ionic surfactant such as Triton x-100, NP-40, tween 20, brij 35, etc. may be used.

The method of improving intracellular specific staining according to the present disclosure may include the above-described procedures, thereby effectively inducing specific staining of target cell organelles and maintaining excellent optical properties.

MODE OF DISCLOSURE

Hereinafter, a method of reducing intracellular non-specific staining and a method of improving specific staining according to the present disclosure will be described in more detail with reference to Examples and Comparative Examples. However, it is apparent to those skilled in the art that these Examples are for illustrative purposes only, and the technical scope of the present disclosure is not intended to be limited by these Examples.

Example 1—Reduction of Non-Specific Staining (Verification of Effectiveness of Blocking)

To verify effectiveness of blocking of active sites, the following procedures (1) to (3) were performed.

(1) BSC-1 cells were fixed with a 4% formaldehyde solution at 4° C. for about 15 minutes, and then washed with a phosphate buffer solution twice.

(2) Intracellular active sites of the cells prepared in the procedure (1) were blocked with potassium hexacyanoferrate(III) for about 20 minutes, and the potassium hexacyanoferrate(III) was washed with a phosphate buffer solution.

(3) Thereafter, 300 nM of silver nanocluster (615 emitter) protected with 5'-CGCGC$_{12}$CGCG-3' (SEQ ID NO:1) was added to the cells that had undergone the procedures (1) and (2), followed by incubation at 4° C. overnight.

Example 2—Specific Tubulin Staining Including Blocking

Specific cell organelle staining including the following procedures (1) to (6) was performed.

(1) BSC1 cells were fixed with a 4% formaldehyde solution (4° C., 15 minutes).

(2) The previously prepared cells were permeated with Triton X-100 (0.5%) (4° C., 4 minutes).

(3) The previously prepared cells were washed with PBS three times, and then labeled with biotinylated anti-alpha-tubulin antibody (50 μg dissolved in 200 μL phosphate buffered saline (PBS) with 1% BSA) (4° C., overnight).

(4) The previously prepared cells that had undergone the procedures (1) to (3) were washed with PBS, and then blocked with hexacyanoferrate(III) (20 minutes).

(5) Avidin (460 µg in 650 µL PBS) was added to (4), followed by incubation (room temperature, 2.5 hours).

(6) The above staining was visualized using biotinylated metal complex (200 µL of 5'-biotin 615-emitter (1 µM)) (1 hour).

Comparative Example 1—Specific Staining of Nucleolus in BSC1 Cells

Specific staining of nucleolus in BSC1 cells was induced by the following procedures (1) and (2).

(1) BSC-1 cells were fixed using a 4% formaldehyde solution at 4° C. for about 15 minutes, and then washed with a phosphate buffer solution twice.

(2) 300 nM of silver nanocluster (615 emitter) protected with 5'-CGCGC$_{12}$CGCG-3' (SEQ ID NO:1) was added to the previously prepared cells, followed by incubation at 4° C. overnight.

Comparative Example 2—Tubulin Staining without Blocking

Cell staining was performed in the same manner as in Example 2, except that the blocking of intracellular active sites with potassium hexacyanoferrate(III) for about 20 minutes and the washing of the potassium hexacyanoferrate (III) with the phosphate buffer solution were not included.

Experimental Example and Comparative Experimental Example—Analysis of Results of Cell Staining In all Experimental Examples and Comparative Examples described below, an Olympus X81 epi-fluorescence microscope or a Carl zeiss LSM 710 confocal laser microscope was used to acquire intracellular images (scale bar: 30 µm), and results thereof are shown in FIGS. 1 to 6.

Figure 1:
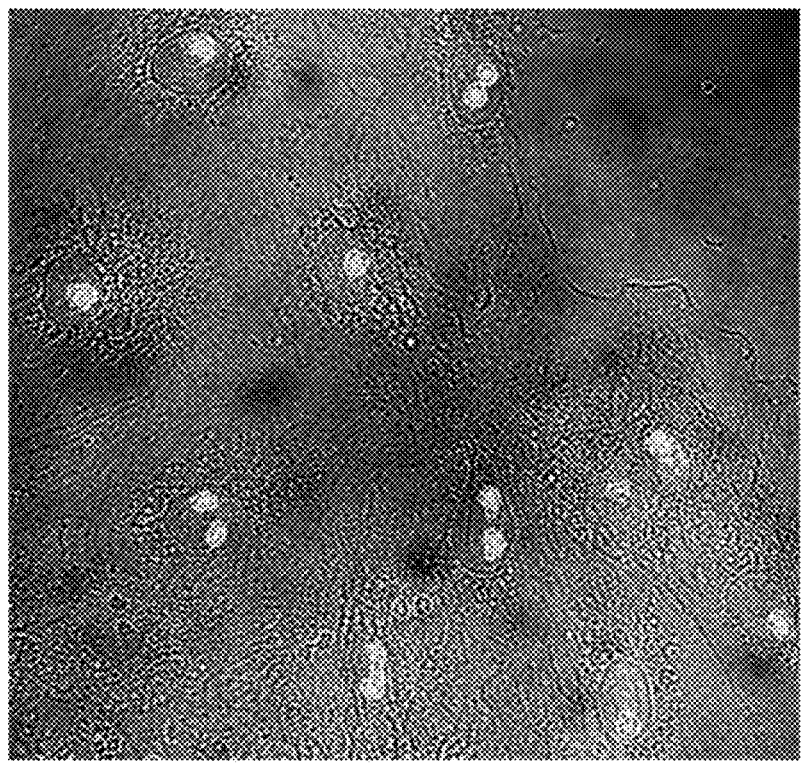
FIGS. 1 and 2 show results of specific staining of intracellular nucleolus of BSC1 using a silver nanocluster (615 emitter) protected with 5'-CGCGC$_{12}$CGCG-3' (SEQ ID NO:1) according to Comparative Example 1 of the present disclosure.
Figure 2:
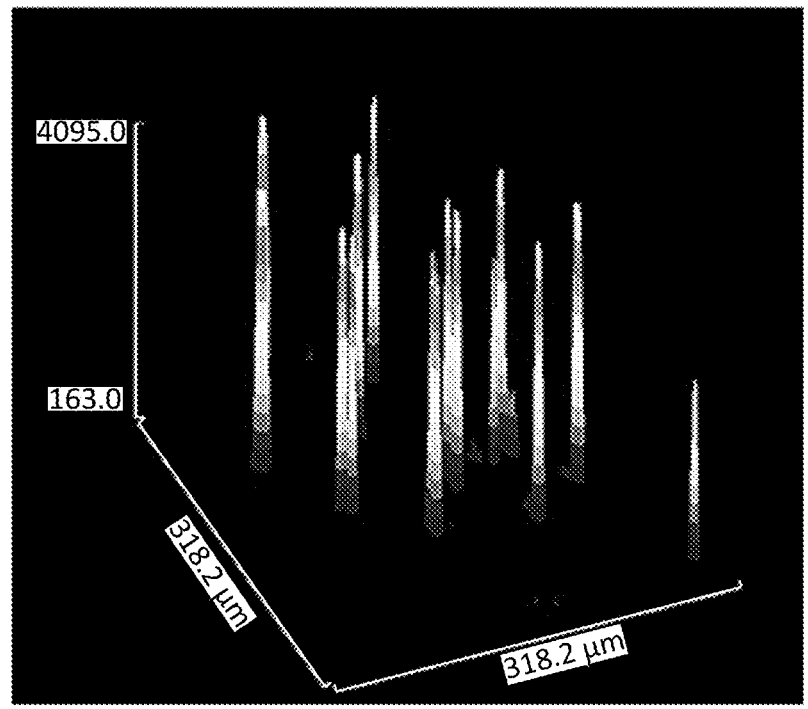

In detail, FIG. 1 shows bright field and emission image of BSC1 cells according to Comparative Example 1 of the present disclosure, and FIG. 2 shows a surface profile image of the emission image of FIG. 1.

As shown in FIGS. 1 and 2, it was confirmed that when the BSC1 cell staining method according to Comparative Example 1 of the present disclosure was used, excellent nucleolus-specific cell staining properties having a signal-to-noise ratio of 40±2 were obtained.

Further, FIG. 3 shows bright field and emission image of BSC1 cells according to Example 1 of the present disclosure, and FIG. 4 shows a surface profile of the emission image of FIG. 3. As shown in FIGS. 3 and 4, it was confirmed that when the BSC1 cell staining method including blocking according to Example 1 of the present disclosure was used, nucleolus-specific staining was effectively blocked. Indirectly, it was confirmed that when blocking of intracellular active sites by oxidation of sulfhydryl groups is performed, intracellular non-specific staining by metal complexes may be effectively reduced.

Experimental Example 2—Examination of Specific Staining Properties According to Presence of Blocking To examine cell staining properties according to the presence of blocking, the Olympus X81 epi-fluorescence microscope or the Carl zeiss LSM 710 confocal laser microscope was used to acquire intracellular images (scale bar: 30 µm) according to Example 2 and Comparative Example 2, and results thereof are shown in FIGS. 5 and 6.

As shown in FIG. 5, it was confirmed that when cell staining including blocking according to Example 2 was induced, the blocking effectively blocked non-specific staining in BSC1 cells, and at the same time, successfully induced specific staining of target tubulin.

In contrast, as shown in FIG. 6, it was confirmed that when cell staining according to Comparative Example 2 was performed, specific staining of target tubulin was not successfully induced due to non-specific staining.

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: a protecting group of the metal complex

<400> SEQUENCE: 1 cgcgccccc cccccccgcg                                              20
```

Experimental Example 1. Examination of Staining Properties According to Presence of Blocking in Cell Staining Using 615-Emitter To examine cell staining properties according to the presence of blocking, the Olympus X81 epi-fluorescence microscope or the Carl zeiss LSM 710 confocal laser microscope was used to acquire intracellular images (scale bar: 30 µm) according to Example 1 and Comparative Example 1, and results thereof are shown in FIGS. 1 to 4.

The invention claimed is:

1. A method of reducing intracellular non-specific staining compared to staining without blocking, the method comprising blocking intracellular active sites by oxidizing intracellular sulfhydryl groups, wherein effectiveness of the blocking is demonstrated according to intracellular staining of a metal complex having a specific staining ability for intracellular nucleolus.

2. The method of reducing intracellular non-specific staining of claim 1, wherein the metal complex is a silver nanocluster comprising 5'-CGCGC$_{12}$CGCG-3' (SEQ ID NO:1) as a protecting group.

3. The method of reducing intracellular non-specific staining of claim 1, wherein the blocking of the intracellular active sites comprises converting the sulfhydryl groups into disulfide using potassium hexacyanoferrate(III), potassium periodate, osmium tetroxide, or iodine.

4. A method of improving intracellular specific staining compared to staining without blocking, the method comprising blocking intracellular active sites by oxidizing intracellular sulfhydryl groups; and inducing staining of intracellular specific sites using metal complexes.

5. The method of improving intracellular specific staining of claim 4, wherein the blocking of the intracellular active sites comprises converting the sulfhydryl groups into disulfide using potassium hexacyanoferrate(III), potassium periodate, osmium tetroxide, or iodine.

6. The method of improving intracellular specific staining of claim 4, wherein the metal complex comprises a transition metal or a member of the lanthanides group.

7. The method of improving intracellular specific staining of claim 4, wherein the metal complex comprises a metal core; and a ligand protecting the metal core.

8. The method of improving intracellular specific staining of claim 7, wherein the ligand is a peptide, DNA, ssDNA or biotinylated ssDNA, a cyclen derivative, a bipyridine derivative, or a terpyridine derivative.

9. The method of improving intracellular specific staining of claim 8, wherein, when the ligand is a biotinylated ssDNA, the method further comprises labelling the target with biotinylated antibody in the cells and binding avidin, and the blocking of intracellular active sites is performed after the labelling and before the binding.

10. The method of improving intracellular specific staining of claim 4, further comprising permeating the cells with a surfactant.

* * * * *